US00PP26591P2

(12) United States Plant Patent
Deng et al.

(10) Patent No.: US PP26,591 P2
(45) Date of Patent: Apr. 5, 2016

(54) ***CALADIUM* PLANT NAMED 'SIZZLE'**

(50) Latin Name: *Caladium×hortulanum*
Varietal Denomination: Sizzle

(71) Applicant: Florida Foundation Seed Producers, Inc., Marianna, FL (US)

(72) Inventors: Zhanao Deng, Riverview, FL (US); Brent K. Harbaugh, Bradenton, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 14/756,217

(22) Filed: Aug. 19, 2015

(51) Int. Cl.
*A01H 5/12* (2006.01)

(52) U.S. Cl.
USPC ..... Plt./373

(58) Field of Classification Search
USPC ..... Plt./373
See application file for complete search history.

*Primary Examiner* — Keith Robinson
(74) *Attorney, Agent, or Firm* — Christopher & Weisberg, P.A.

(57) ABSTRACT

A new and distinct cultivar of *Caladium* plant named 'Sizzle', characterized by its mounding growth habit, heart-shaped leaves that have a large red center, dark red to purple mid and primary veins, netted greyed-purple secondary veins, and mottled undulate margins, and plants that are attractive in containers or in sunny or shady landscapes.

8 Drawing Sheets

ACKNOWLEDGEMENT OF FEDERAL RESEARCH SUPPORT

This invention was made with government support under FLA-BRA-04162 awarded by the Cooperative State Research, Education, and Extension Service, USDA and under FLA-GCR-005065 awarded by the National Institute of Food and Agriculture, USDA. The government has certain rights in the invention.

Genus and species: *Caladium×hortulanum.*

Cultivar denomination: 'Sizzle'.

CROSS-REFERENCE TO RELATED APPLICATION n/a

BACKGROUND OF THE NEW CULTIVAR

The present invention relates to a new and distinct cultivar of *Caladium* plant, botanically known as *Caladium×hortulanum*, commercially referred to as a strap leaf-type or lance leaf-type *Caladium* and hereinafter referred to by the name 'Sizzle'.

*Caladiums* (also referred to as *Caladium* plants) are ornamental aroids frequently used as pot and landscape plants for their colorful foliage and ease of growing. The objective of the Inventors' breeding program is to create new *Caladium* cultivars that have compact growth habit, numerous leaves, attractive foliage, and exceptional container and landscape performance.

The new *Caladium* cultivar 'Sizzle' originated from a cross between '*Candidum* Junior' (commercial cultivar, not patented) and 'Florida Sweetheart' (U.S. Plant Pat. No. 8,526) that was made in Bradenton, Fla., in spring 2003. The new *Caladium* cultivar 'Sizzle' was discovered and selected by the inventors as a single plant in Bradenton, Fla. in 2004. The *Caladium* cultivar 'Sizzle' has been found to retain its distinctive characteristics through at least nine generations of successive asexual propagations conducted in Wimauma, Fla. via tuber divisions since 2004.

Plant Breeder's Rights for this cultivar have not been applied for. 'Sizzle' has not been made publicly available more than one year prior to the filing of this application.

SUMMARY OF THE INVENTION

The new *Caladium* cultivar has not been observed under all possible environmental conditions. The phenotype may vary somewhat with variations in environment such as temperature, light intensity, water status, fertilizer rate and type, without, however, any variance in genotype.

The following are the most outstanding and distinguishing characteristics of this new *Caladium* cultivar when grown under (normal or standard) horticultural practices in Wimauma, Fla. The combination of these characteristics distinguishes 'Sizzle' as a new and distinct cultivar of *Caladium:*

1. Symmetrical, outwardly arching and rounded plant form;
2. Mounding, dense and bushy growth habit;
3. Heart-shaped leaves that have a large rose center, numerous dark red to purple primary veins, netted purple secondary veins throughout the leaf, and mottled undulate margins; and
4. Attractive plants in containers or in sunny or shady landscapes.

The new *Caladium* cultivar 'Sizzle' differs from its female parent, '*Candidium* Junior' in the following characteristics:

1. Leaves of 'Sizzle' are of the lance or strap type with the petiole attached to the base of leaves, whereas the leaf of '*Candidum* Junior' has a petiole attached to the back of the leaf; and
3. Leaves of 'Sizzle' have a large red center and dark red primary veins, whereas leaves of '*Candidium* Junior' have green veins and white interveinal areas.

The new *Caladium* cultivar 'Sizzle' differs from its male parent, 'Florida Sweetheart' (U.S. Plant Pat. No. 8,526), in the following characteristics:

1. The mid and primary veins on leaves of 'Sizzle' are dark red to greyed purple, whereas the mid and primary veins on leaves of 'Florida Sweetheart' are light rose to rose;
2. The primary veins on leaves of 'Sizzle' are thicker and more prominent than the primary veins on leaves of 'Florida Sweetheart';
3. The interveinal areas near the center of leaves of 'Sizzle' are dark rose (when plants were grown in shady locations) and dark red to purple (when plants were grown in full sun), whereas the interveinal areas near the center of leaves of 'Florida Sweetheart' are light rose (in shady locations) and rose (in full sun);
4. The apex of leaves of 'Sizzle' is longer and more pointed than the apex of 'leaves of 'Florida Sweetheart'; and
5. The surface and the cortical area of tubers of 'Sizzle' are brown and yellow, respectively, whereas the surface and the cortical area of tubers of 'Florida Sweetheart' are light brown and light yellow, respectively.

The new *Caladium* cultivar 'Sizzle' can also be compared to the *Caladium* cultivar 'UF 4412' (U.S. Plant Pat. No. 25,612). In side-by-side comparisons conducted in Wimauma, Fla., plants of the new *Caladium* cultivar differed from plants of 'UF 4412' *Caladium* in the following characteristics:

1. Plants of 'Sizzle' were shorter with a more compact growth habit than plants of 'UF 4412';
2. Leaves of 'Sizzle' were smaller and narrower than leaves of 'UF 4412';
3. Leaves of 'Sizzle' have distinctive netted veins of dark red to greyer purple, whereas leaves of 'UF 4412' have pink to red veins; and
4. Leaves of 'Sizzle' have a redder colored center, whereas leaves of 'UF 4412' have a more pinkish colored center.

DESCRIPTION OF THE FIGURES

The accompanying photographs (as shown in FIGS. 1-8) illustrate the overall appearance of the new *Caladium* cultivar. These photographs show the colors as true as can be reasonably obtained in colored reproductions of this type. Colors in the photographs may differ slightly from the color values cited in the detailed botanical description, which accurately describe the colors of the new *Caladium* cultivar.

DETAILED BOTANICAL DESCRIPTION

Figure 1:
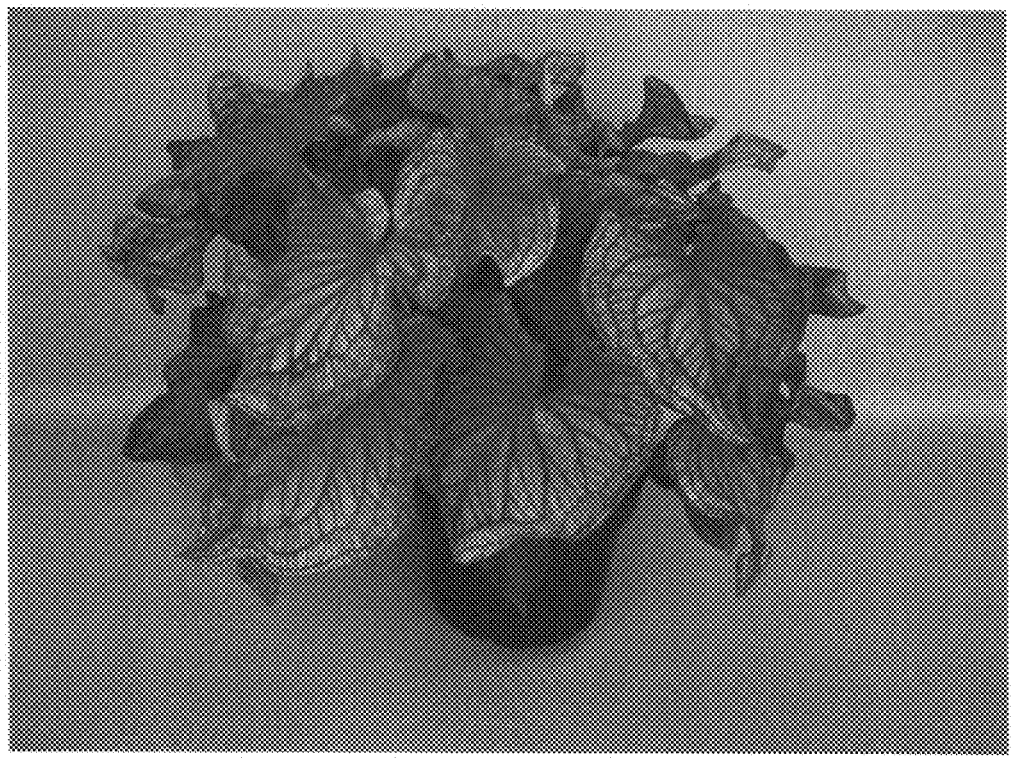
FIG. 1 shows a photograph of a side view of a typical plant of 'Sizzle' grown in a 20-cm diameter container in a shadehouse.
Figure 2:
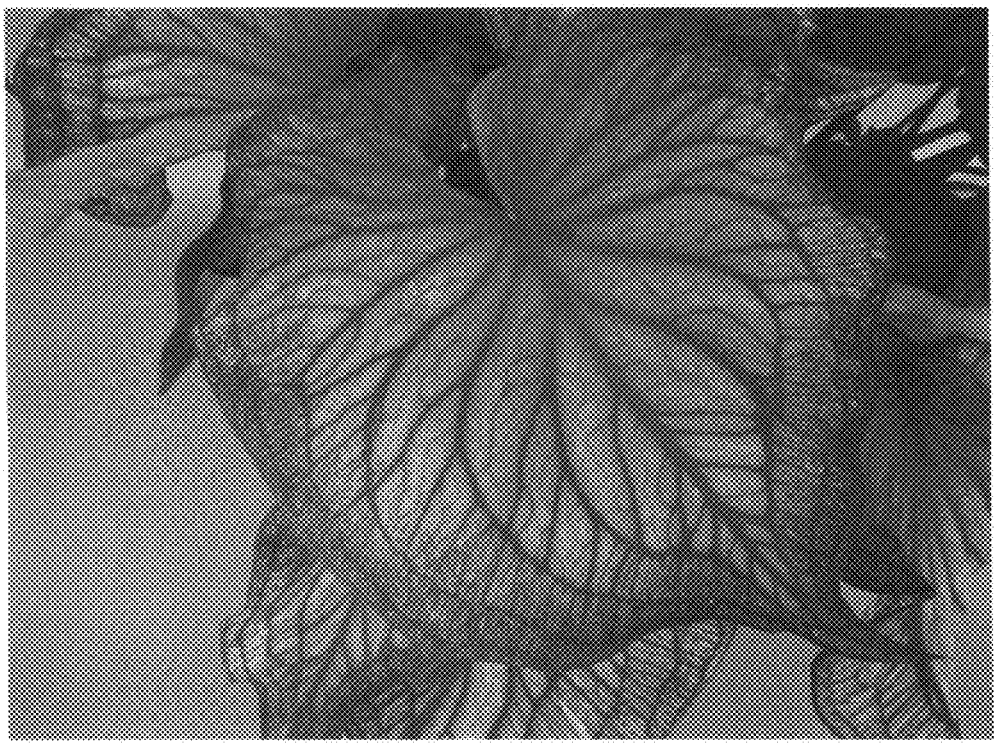
FIG. 2 shows a photograph of a top view of a typical leaf of 'Sizzle' grown in a 20-cm diameter container in a shadehouse.
Figure 3:
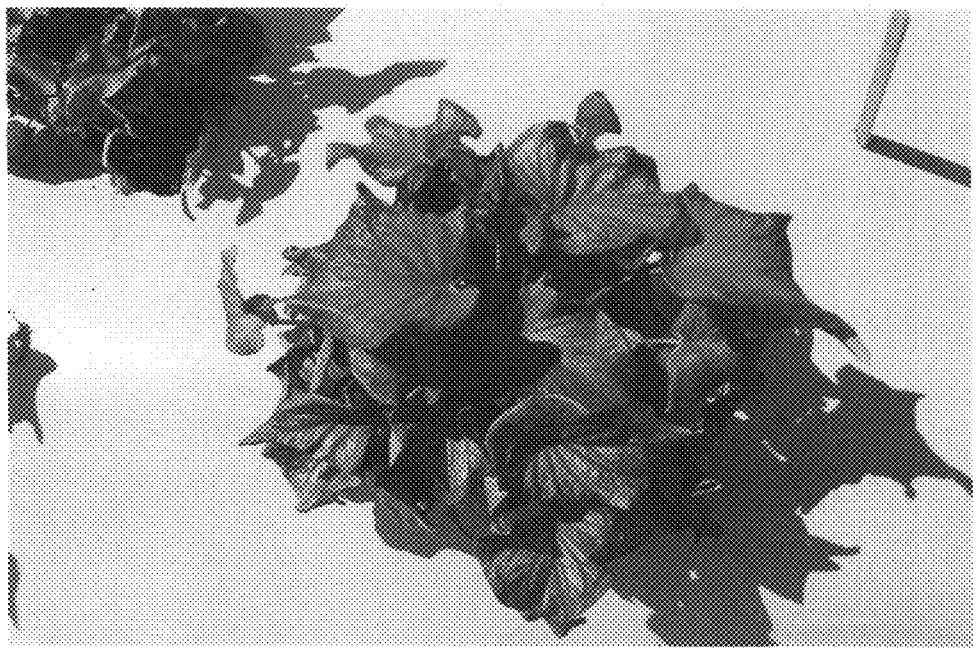
FIG. 3 shows a photograph of a top view of typical plants of 'Sizzle' grown in an outdoor nursery.
Figure 4:
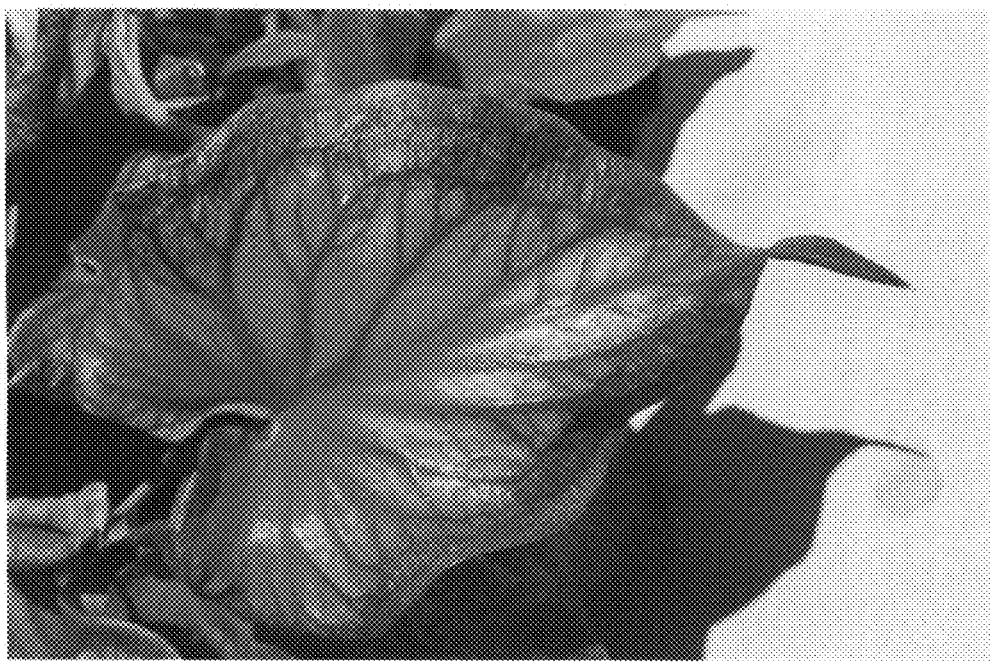
FIG. 4 shows a photograph of a top view of a typical leaf of 'Sizzle' grown in an outdoor nursery.
Figure 5:
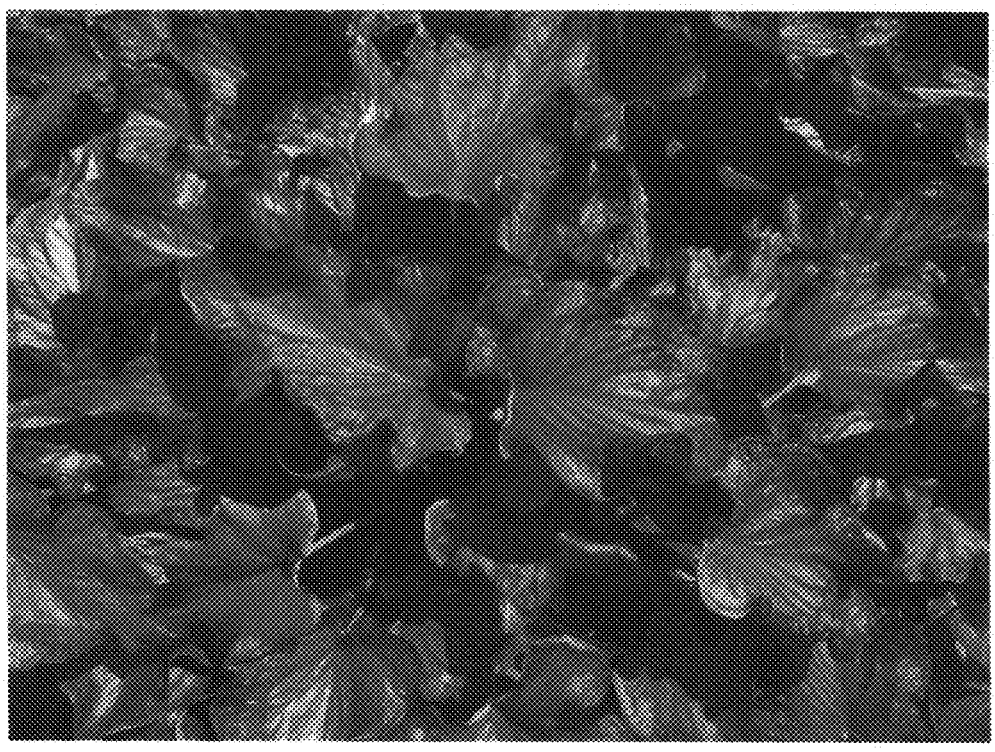
FIG. 5 shows a photograph of a top view of typical plants of 'Sizzle' grown in an outdoor nursery for approximately five months.
Figure 6:
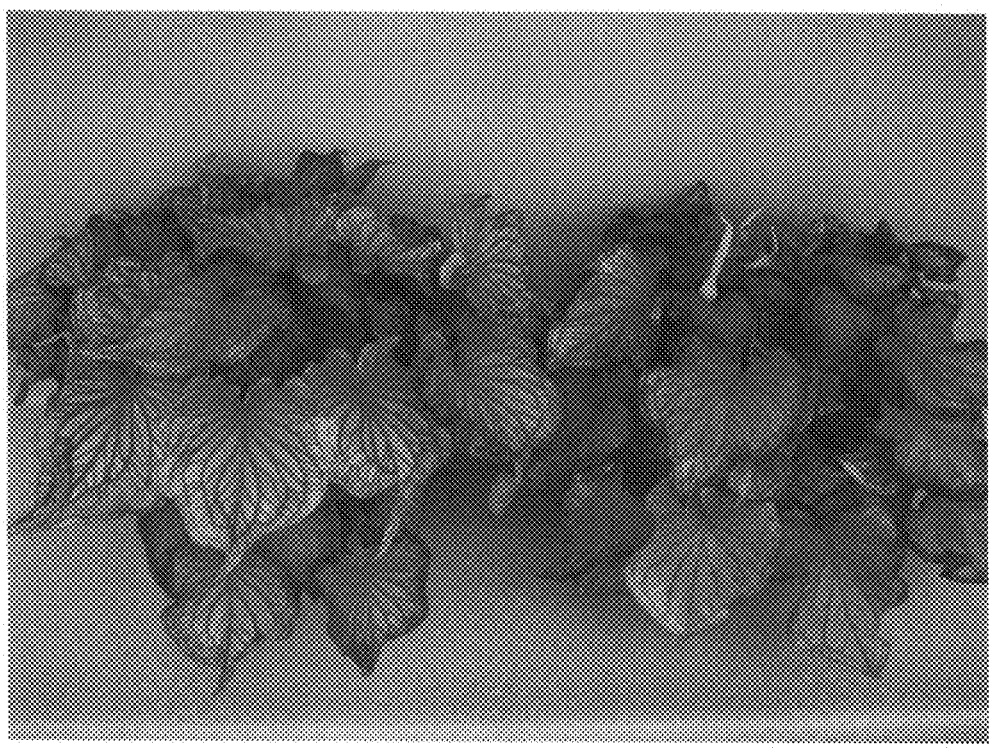
FIG. 6 shows a photograph of a side view of typical plants of 'Sizzle' (left) and 'Florida Sweetheart' (right) grown in 20-cm diameter container in a shadehouse.
Figure 7:
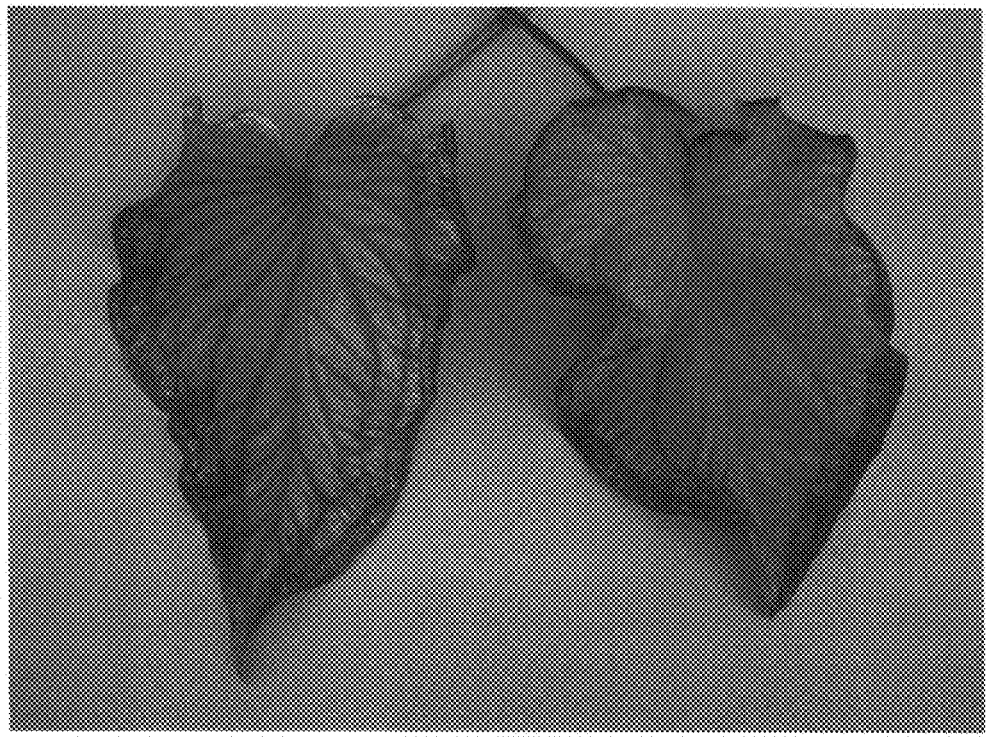
FIG. 7 shows a photograph of a top view of typical leaves of 'Sizzle' (left) and 'Florida Sweetheart' (right) grown in 20-cm diameter container in a shadehouse.
Figure 8:
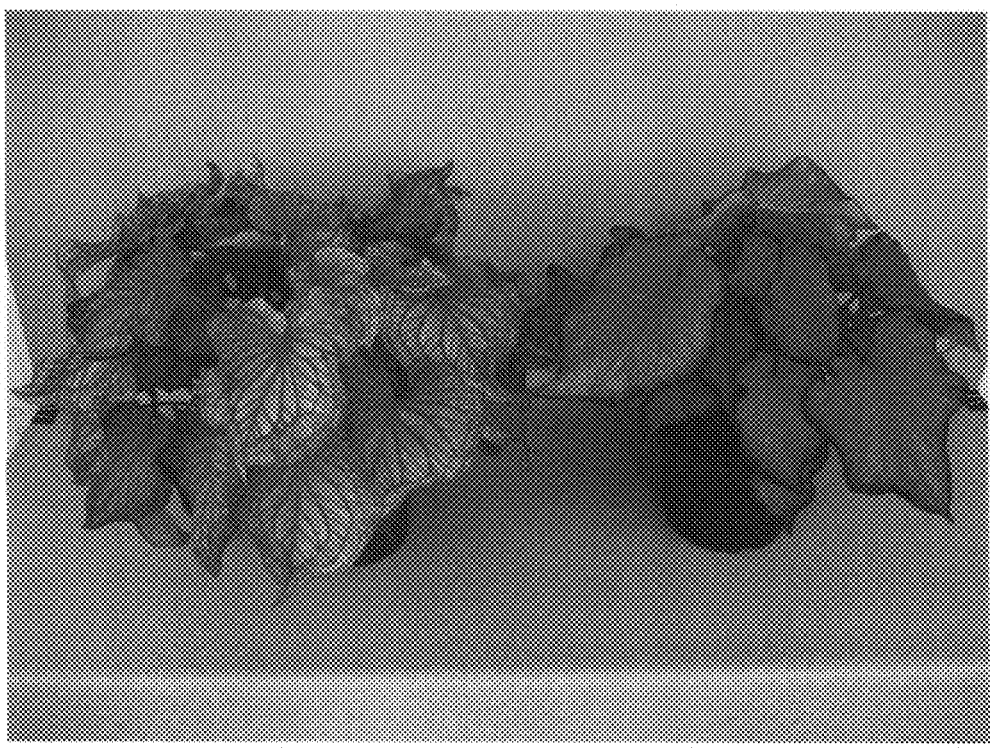
FIG. 8 shows a photograph of a side view of typical plants of 'Sizzle' (left) and 'UF 4412' (right) grown in 20-cm diameter container in a shadehouse.

In the following description, color references are made to The Royal Horticultural Society (R.H.S.) Colour Chart, 1986 Edition, except where general terms of ordinary dictionary significance are used. The features of 'Sizzle' described herein are shown in FIGS. 1-8.

Description of Growing Conditions

The following observations and measurements describe plants grown in 20-cm containers in Wimauma, Fla., during the summer in a polypropylene-covered shadehouse and plants grown in ground beds in Wimauma, Fla., during the late summer in an outdoor nursery. All plants were grown under conditions and practices similar to those generally used in commercial *Caladium* production.

During the production of the plants, day temperatures ranged from approximately 21.7° F. to 33.6° F., night temperatures ranged from approximately 66.5° F. to 76.1° F., and light levels were approximately 944 foot-candles in the shadehouse and 9744 foot-candles in the outdoor nursery. Plants grown in the shadehouse were approximately seven weeks from planting tubers when the photographs and the detailed description were taken. Plants grown in the outdoor nursery were approximately two months from planting tubers when the photographs and the detailed description were taken.

Botanical Description

Botanical classification:

*Family*.—Araceae.

*Botanical name*.—*Caladium×hortulanum*.

*Common name*.—*Caladium*.

*Cultivar*.—'Sizzle' (*Caladium×hortulanum* cultivar 'Sizzle').

Parentage:

*Female or seed parent*.—'*Candidum* Junior'.

*Male or pollen parent*.—'Florida Sweetheart' (U.S. Plant Pat. No. 8,526).

Propagation:

*Type*.—By tubers and by tuber divisions.

*Time to initiate roots, summer*.—Approximately seven to ten days at 32° C.

*Time to initiate roots, winter*.—Approximately two to three weeks at 24° C.

Tuber description: Jumbo-sized (6.4 to 8.9 cm in diameter) tubers are multi-segmented, bearing six to nine dominant buds.

*Height of tubers*.—2 to 3 cm.

*Diameter of tubers*.—Up to 11.4 cm.

*Texture*.—Thick, starchy inside; slightly brittle between tuber segments.

*Color*.—Epidermis, close to brown (RHS 200B); Interior, yellow (RHS 7B).

*Root description*.—Dense, thick and yellow-white (RHS 159C) fleshy roots.

Plant description:

*Type*.—Herbaceous perennial.

*Plant form*.—Upright, outwardly arching and symmetrical plant.

*Growth habit*.—Compact and mounding, dense foliage, suitable for containers with 10.0 cm or larger diameters. Leaf petioles arising from tubers; petioles mostly semi-upright and curving outwardly with development.

*Plant height, from soil level to top of leaf plane, shadehouse-grown plants*.—Approximately 37 cm.

*Plant height, from soil level to top of inflorescences, shadehouse-grown plants*.—Approximately 30 cm.

*Plant spread, shadehouse-grown plants*.—Approximately 60 cm×57 cm.

*Plant height, from soil level to top of leaf plane, outdoor nursery-grown plants*.—Approximately 22 cm to 27 cm.

*Plant height, from soil level to top of inflorescences, outdoor nursery-grown plants*.—None observed

*Plant spread, outdoor nursery-grown plants*.—Approximately 45 cm×41 cm.

Foliage description (shadehouse-grown and outdoor-grown):

*Length, shadehouse-grown plants*.—Approximately 20 cm.

*Width, shadehouse-grown plants* (*flattened*).—Approximately 16 cm.

*Length, outdoor nursery-grown plants*.—Approximately 14 cm.

*Width, outdoor nursery-grown plants* (*flattened*).—Approximately 9 cm.

*Shape*.—Ovate.

*Apex*.—Acuminate to acute.

*Base*.—Cordate.

*Margin*.—Entire; undulate.

*Texture, upper surface*.—Smooth, glabrous.

*Texture, lower surface*.—Smooth, glabrous, glaucous.

*Venation pattern*.—Pinnate.

Leaf color, shadehouse-grown plants:

*Fully expanded leaves*.—Upper surface: Center: Close to red (RHS 51A to 51B). Border and margins: Close to green (RHS 139A), with specs of white (RHS 155A) and green (RHS 139A). Basal notch: none. Venation: Midrib: Close to red (RHS 53C). Primary: Close to greyed-purple (RHS 183A). Lower surface: Center: Close to red (RHS 51B). Border and margins: Close to greyed-green (RHS 191A), with specs of yellow-white (RHS 158C). Venation: Midrib: Close to greyed-red (RHS 182C). Primary veins: Close to green (RHS 137B to 137D).

Leaf color, outdoor nursery-grown plants:

*Developing leaves*.—Upper surface: Center: Close to red (RHS 53C and 53D). Border and margins: Close to green (RHS 137A), with mottling of yellow-white (RHS 158C). Venation: Midrib: Close to red (RHS 53A). Primary: Close to greyed-purple (RHS 185A). Lower surface: Center: Close to red-purple (RHS 60B), with mottling of white (RHS 155A). Border and margins: Close to greyed-green (RHS 191A), with mottling of greyed-yellow (RHS161C). Venation: Midrib: Close to greyed-yellow (RHS 161B) with streaks of greyed-red (RHS 182A). Primary: Close to greyed-yellow (RHS 161D) to the outer tips of greyed-green (RHS 194C).

*Fully expanded leaves*.—Upper Surface: Center: Close to red (RHS 53C and 53D). Border and margins: Close to green (RHS 137A), with mottling of greyed-yellow (RHS 161D). Venation: Midrib: Close to red purple (RHS 60A). Primary: Close to greyed-purple (RHS 183A) to greyed-purple (RHS 187A) near the margins. Lower surface: Center: Close to greyed-purple (RHS 185C). Border and margins: Close to greyed-green (RHS 191A), with mottling of yellow-white (RHS 158B). Venation: Midrib: Close to greyed-yellow (RHS 161B) with numerous streaks of greyed-red (RHS 181A). Primary: Close to greyed-yellow (RHS 161D) to greyed-green (RHS 194A) near margins.

Petiole:

*Aspect*.—Mostly erect, curving outwardly with development.

*Length, shadehouse-grown plants*.—Approximately 21 to 26 cm.

*Diameter, distal, shadehouse-grown plants*.—Approximately 4.6 mm.

*Diameter, proximal, shadehouse-grown plants*.—Approximately 8.3 mm.

*Length, outdoor nursery-grown plants*.—Approximately 16.0 cm to 19.0 cm.

*Diameter, distal, outdoor nursery-grown plants*.—Approximately 3.4 mm.

*Diameter, proximal, outdoor nursery-grown plants*.—Approximately 6.2 mm.

*Strength*.—Strong; flexible.

*Color, shadehouse-grown plants*.—Generally close to greyed-red (RHS 179B or 179D) with speckling or streaks of brown (RHS 200C and 200D).

*Color, proximal, outdoor nursery-grown plants*.—Close to brown (RHS 200D) with streaks of brown (RHS 200A or 200C).

*Wing length, shadehouse-grown plants*.—Approximately 3.0 cm to 4.0 cm.

*Wing diameter, shadehouse-grown plants*.—Approximately 6.7 mm to 7.7 mm.

*Wing length, outdoor nursery-grown plants*.—Approximately 4.4 cm to 5.2 cm.

*Wing diameter, outdoor nursery-grown plants*.—Approximately 5.9 mm to 7.4 mm.

*Wing color, shadehouse-grown plants*.—Close to greyed-red (RHS 182D) with streaks and blotches of brown (RHS 200C).

*Wing color, outdoor nursery-grown plants*.—Close to greyed-red (RHS 179D but much lighter) with streaks of brown (RHS 200C).

Inflorescence description (plants of 'Sizzle' produce inflorescences only occasionally):

*Inflorescence arrangement*.—Upright hooded spathes surrounding a columnar spadix borne on an upright scape. Spadix carries sessile, simple female and male flowers separated into two zones. Female flowers arranged on the lower one-third of the spadix; male flowers arranged on the upper two-thirds of the spadix. Sterile flowers develop between female and male flower zones. Spadix constricts near the sterile flower zone.

*Fragrance*.—None detected.

*Natural flowering season/longevity*.—Plants of 'Sizzle' typically flower during spring or early summer in central Florida. Flowers develop about seven weeks after growth commence. Inflorescences last about four days before fading.

*Spathe*.—Length: Approximately 10.5 cm. Width: Distal: Approximately 2.3 cm. Proximal: Approximately 2 cm. Shape: Ovate to somewhat obovate. Apex:

Acute to acuminate. Base: Tapering. Margin: Entire. Texture: Upper and lower surfaces: Smooth, glabrous. Color: Front surface: Upper two-thirds: Close to yellow- white (RHS 158D). Lower one-third: Close to green (RHS 144B) with streaks of green-white (RHS 157). Rear surface: Upper two-thirds: Close to green-white (RHS 157A) with blotches of green (RHS 144C). Lower one-third: Close to green-white (RHS 157D) with streaks of green (RHS 144B).

*Spadix*.—Length, entire spadix: Approximately 6 cm. Length, male flower zone: Approximately 3.5 cm. Length, sterile flower zone: Approximately 1 cm. Length, female flower zone: Approximately 1.5 cm. Diameter, male flower zone: Approximately 8 mm. Diameter, sterile flower zone: Approximately 6.5 mm. Diameter, female flower zone: Approximately 9 mm. Shape: Spindle-shaped to columnar. Apex: Obtuse. Base: Obtuse. Aspect: Upright. Color, mature, male zone: Close to yellow-white (RHS 158A). Color, mature, sterile zone: Close to yellow (RHS 155B). Color, mature, female zone: Close to greyed-yellow (RHS 162A). Male flowers: Quantity per spadix: Approximately 94. Shape: Obovate. Height: Approximately 3.5 mm. Diameter: Approximately 2.5 mm. Pollen color: Close to yellow (RHS 10B). Amount of pollen: Scant. Female flowers: Quantity per spadix: Approximately 112. Shape: Obovate. Height: Approximately 1 mm. Diameter: Approximately 1 mm.

*Shape*.—Length: Approximately 12.8 cm. Diameter: Approximately 5.6 mm. Strength: Sturdy, flexible. Aspect: Erect. Texture: Smooth, glabrous, glaucous. Color, proximal: Close to greyed-brown (RHS 199B) with streaks of brown (RHS 200C). Just below spathe: Close to green (RHS 144A).

*Seed and fruit*.—Seed and fruit development has not been observed on inflorescences that were not hand-pollinated.

Disease/pest resistance: Plants of 'Sizzle' have been observed to be somewhat resistant to *Xanthomonas* leaf spot.

Temperature tolerance: Tolerant to temperatures ranging from approximately 7° C. to approximately 40° C.

Sunburn tolerance: Moderate to high levels of tolerance to sunburns.

Comparison with Known Cultivars

'Sizzle' was evaluated for tuber production at the Gulf Coast Research and Education Center in Wimauma, Fla. in 2007, 2008, and 2009. The soil was EauGallie fine sand with about 1% organic matter and a pH value between 6.2 and 7.4. *Caladium* plants were grown in the field using a plastic-mulched raised-bed system. For the 2007 evaluation, ground beds (81 cm wide, 20 cm high) were fumigated on 3 April with a mixture of 67% methyl bromide and 33% chloropicrin (by volume) at the rate of 196 kg·ha$^{-1}$. *Caladium* seed pieces (tuber pieces, approximately 2.5×2.5×2.5 cm) were planted manually on 26 April with approximately 25.4 cm between-row spacing and approximately 15.2 cm in-row spacing. Drip tapes were buried under the plastic mulch and delivered approximately 6 mm of water to the bed per day. Fertigation (through the drip irrigation system) began when young *Caladium* plants emerged from the soil, supplying soluble fertilizer (6N-0.8P-3.9K) at the rate of approximately 1.9 kg of nitrogen·ha$^{-1}$·day$^{-1}$ and a total 290 kg of nitrogen·ha$^{-1}$ per growing season. Tubers (new crop) were dug, washed, and dried in early January 2008. Dried tubers from each experimental field plot were weighed, graded, and counted in late January 2008. Tuber grading was by the tuber maximum diameter: Super Mammoth (greater than 11.4 cm), Mammoth (8.9 to 11.4 cm), Jumbo (6.4 to 8.9 cm), No.1 (3.8 to 6.4 cm), and No. 2 (2.5 to 3.8 cm). Tuber grades and counts were converted into a Production Index (PI) to show the relative economic value of the harvested tubers per field plot: PI=8n (Supper Mammoth)+6n (Mammoth)+4n (Jumbo)+2n (No.1)+1n (No.2), where n=number of tubers in the grade. The relative values assigned to the five tuber grades in calculating PIs were based on the relative market prices provided by Florida *Caladium* tuber producers.

For the 2008 evaluation, beds were fumigated with a mixture of 80% methyl bromide and 20% chloropicrin (by volume) at the rate of 448 kg·ha$^{-1}$. *Caladium* seed pieces were planted on 18 Apr. 2008 at approximately 15-cm spacing between and within rows. The irrigation and fertigation system was the same as the one used in 2007. Tubers were dug from 2 to 8 Dec. 2009, followed by washing, drying, weighing, grading, and counting as done in 2007.

For the 2009 evaluation, beds were fumigated on 27 February with a mixture of 50% methyl bromide and 50% chloropicrin (by volume) at the rate of 196 kg·ha$^{-1}$. *Caladium* seed pieces were planted on 9 Apr. 2009 at approximately 15-cm spacing between rows and in rows. The irrigation and fertigation system was the same as the one used in 2007, but one teaspoon (approximately seven grams) of OSMOCOTE® controlled-release fertilizer (15N-2.6P-10K, 5-6 months) was applied to each plant on 21 July. Tubers were dug from 30 November to 2 December 2009, followed by washing, drying, weighing, grading, and counting as was done in 2007.

Field plots were arranged each season in three randomized complete blocks, and each plot (1.2 m$^2$) was planted with 30 *Caladium* seed pieces. Two commercial cultivars, 'Florida Red Ruffles' (U.S. Plant Pat. No. 13,136) and 'Florida Sweetheart', were included as controls in each block. Analyses of variance were conducted using the PROC GLM procedure in SAS (SAS Institute, Cary, N.C.) to compare the tuber yields of 'Sizzle' to that of 'Florida Red Ruffles' and 'Florida Sweetheart'.

Table 1 shows the tuber weight, marketable tubers, production index, and grade distribution of 'Sizzle' grown in Wimauma, Fla. in 2007, 2008, and 2009. Values presented for each year are means of three plots in three randomized complete blocks.

TABLE 1

| | Tuber | | |
|---|---|---|---|
| Cultivars | Weight (kg) | Marketable (no.) | Production index$^z$ |
| | Year 2007 | | |
| Sizzle | 3.6$^{NS}$ | 53.7$^{NS}$ | 134.3$^{NS}$ |
| Florida Red Ruffles | 2.7 | 42.2 | 84.4 |
| Florida Sweetheart | 3.3 | 45.6 | 104.9 |
| | Year 2008 | | |
| Sizzle | 3.5 a | 60.0$^{NS}$ | 136.0 a |
| Florida Red Ruffle | s1.5 b | 50.1 | 81.1 b |
| Florida Sweetheart | 1.9 b | 53.3 | 88.0 b |

TABLE 1-continued

| | Year 2009 | | |
|---|---|---|---|
| Sizzle | 2.5 a | 32.3 ab | 83.3 a |
| Florida Red Ruffles | 0.9 b | 24.7 b | 38.0 b |
| Florida Sweetheart | 2.7 a | 47.0 a | 94.7 a |

| | Tuber grade distribution (%) | | | | |
|---|---|---|---|---|---|
| Cultivars | Super Mammoth | Mammoth | Jumbo | No. 1 | No. 2 |
| | Year 2007 | | | | |
| Sizzle | | 7.0$^{NS}$ | 22.3$^{NS}$ | 41.4 a$^{y}$ | 29.4$^{NS}$ |
| Florida Red Ruffles | | 1.0 | 20.0 | 41.0 a | 37.9 |
| Florida Sweetheart | | 2.6 | 28.6 | 31.3 b | 37.5 |
| | Year 2008 | | | | |
| Sizzle | | | 26.1 a | 50.6$^{NS}$ | 23.3 b |
| Florida Red Ruffle | | | 3.9 b | 51.5 | 44.6 a |
| Florida Sweetheart | | | 17.4 ab | 64.9 | 17.8 b |
| | Year 2009 | | | | |
| Sizzle | | 5.3 a | 27.8 a | 50.4$^{NS}$ | 16.5 b |
| Florida Red Ruffles | | 0.0 b | 4.4 b | 32.4 | 63.2 a |
| Florida Sweetheart | | 1.3 ab | 19.5 ab | 38.9 | 40.3 ab |

[z]The production index is an indicator of economic value of the crop harvested and is calculated as: N (No.2s) + 2N (No. 1s) + 4N (Jumbos) + 6N (Mammoth) + 8N (Super Mammoth); where N = number of tubers in each grade. Tubers graded by maximum diameter; No. 2 (2.5 to 3.8 cm), No. 1 (3.8 to 6.4 cm), Jumbo (6.4 to 8.9 cm), Mammoth (8.9 to 11.4 cm), and Super Mammoth (>11 cm).
[y]Mean values with the same letters within columns are not significantly different at P ≤ 0.05.
[NS]not significantly different at P ≤0.05.

As shown in Table 1, 'Sizzle' had a greater tuber weight (3.6 kg vs. 3.3 kg), a larger number of marketable tubers (53.7 vs. 45.6) and a higher PI (134.3 vs. 104.9) than 'Florida Sweetheart' in the 2007 season, but the differences between 'Sizzle' and 'Florida Sweetheart' in tuber weight, number of marketable tubers and PI were not statistically significant. In the 2008 season, 'Sizzle' had an 84.2% greater tuber weight (3.5 kg vs. 1.9 kg) and a 54.5% higher PI (136.0 vs. 88.0) than 'Florida Sweetheart', and differences between 'Sizzle' and 'Florida Sweetheart' in these aspects were statistically significant. In the 2009 season, 'Sizzle' seemed to have a slightly smaller tuber weight (2.5 kg vs. 2.7 kg) and fewer numbers of marketable tubers (32.3 vs. 47.0), and generated a slightly smaller PI (83.3 vs. 94.7), but the differences between 'Sizzle' and 'Florida Sweetheart' in tuber weight, number of marketable tubers and PI were not statistically significant.

As shown in Table 1, the tuber weights of 'Sizzle' were 33.3% (2007), 133.3% (2008), and 177.8% (2009) greater than the tuber weights of 'Florida Red Ruffles' in respective years. The PI of 'Sizzle' was 59.1% (2007), 67.7% (2008), and 118.4% (2009) higher than the PI of 'Florida Red Ruffles' in respective years.

As shown in Table 1, 'Sizzle' and 'Florida Sweetheart' shared similar tuber grade distributions, except that 'Sizzle' produced more No. 1-sized tubers (41.4% vs. 31.3%) in 2007. 'Sizzle' shared the same tuber grade distribution with 'Florida Red Ruffles' in 2007 but produced larger tubers in 2008 and 2009. Compared to 'Florida Red Ruffles', 'Sizzle' produced a higher percentage of Jumbo-sized tubers (26.1% vs. 3.9%) with a lower percentage of No.2-sized tubers (23.3% vs. 44.6%) in 2008, and a higher percentage of Mammoth-sized tubers (5.3% vs. 0), a higher percentage of Jumbo-sized tubers (27.8% vs. 4.4%), with a lower percentage of No.2-sized tubers (16.5% vs. 63.2%) in 2009.

Table 2 shows a comparison of the plant height, number of leaves, leaf length, and leaf width of 'Sizzle' with 'Florida Sweetheart', and 'Florida Red Ruffles', approximately 4 months after planting 2.54-cm tuber pieces (propagules) in ground beds in full sun in 2007 and 2009. Values presented are means of data from three replications and three plants measured per plot per year over two years.

TABLE 2

| Cultivars | Plant height (cm) | Leaves (no.) | Leaf lengthz (cm) | Leaf widthy (cm) |
|---|---|---|---|---|
| 'Sizzle' | 28.0 a$^{x}$ | 28.4$^{Ns}$ | 20.4 a | 12.4 a |
| 'Florida Red Ruffles' | 17.9 c | 27.7 | 16.9 b | 10.0 b |
| 'Florida Sweetheart' | 22.8 b | 28.7 | 19.4 a | 13.4 a |

[z]Leaf length was measured on the largest leaves along the longest line from the leaf lobe to the leaf tip.
[y]Leaf width was measured on the largest leaves across the widest middle part.
[z]Mean values with the same letters within columns are not significantly different at P ≤ 0.05.
NS: not significantly different at P ≤ 0.05.

As shown in Table 2, plants of 'Sizzle' had an average height of 28.0 cm after growing in full sun and sandy soil for about 4 months. Plants of 'Sizzle' were about 5 to 10 cm taller than plants of 'Florida Red Ruffles' or 'Florida Sweetheart'. Leaves of 'Sizzle' had an average size of 20.4 cm by 12.4 cm and were approximately 3.5 cm longer and approximately 2.4 cm wider than leaves of 'Florida Red Ruffles', but statistically not significantly different from the average leaf size of 'Florida Sweetheart'.

Table 3 shows the landscape performance of 'Sizzle' with 'Florida Sweetheart', and 'Florida Red Ruffles' when planted in ground beds in full sun in 2007, 2008 and 2009. Values presented are means of three replications in each year.

Landscape performance was evaluated on the same plots used for evaluating tuber production. A scale of 1 to 5 was used with 1 being very poor (few leaves and lack of vigor), and 5 being excellent (full plants, numerous leaves, and bright color display). A total of nine evaluations were conducted for plant performance over three growing seasons in July, August, and September 2007, August, September, and October 2008, and August, September, and October 2009.

TABLE 3

| | 2007 | | |
|---|---|---|---|
| Cultivars | July | August | September |
| Sizzle | 4.5 a$^{z}$ | 3.8$^{NS}$ | 3.1$^{NS}$ |
| Florida Red Ruffles | 3.8 b | 3.1 | 2.9 |
| Florida Sweetheart | 3.3 b | 3.1 | 2.8 |
| | 2008 | | |
| Cultivars | August | September | October |
| Sizzle | 4.3 a | 4.3 a | 4.7 a |
| Florida Red Ruffles | 3.1 b | 2.7 b | 2.5 c |
| Florida Sweetheart | 3.3 b | 3.3 b | 3.5 b |

TABLE 3-continued

| Cultivars | 2009 August | 2009 September | 2009 October |
|---|---|---|---|
| Sizzle | 3.2 b | 4.5$^{NS}$ | 4.5 a |
| Florida Red Ruffles | 3.2 b | 3.7 | 3.5 b |
| Florida Sweetheart | 4.7 a | 4.5 | 3.3 b |

[z]Plants were rated on a scale of 1 to 5, with 1 being very poor, 3 fair and acceptable, and 5 being excellent in plant vigor, fullness, and color display, on 27 Jul., 28 Aug., and 15 Sep. 2007; 16 Aug., 1 Sep., and 1 Oct. 2008; and 12 Aug., 15 Sep., and 8 Oct. 2009. Mean values with the same letters within columns are not significantly different at P ≤ 0.05. NS: Not significantly different at P ≤ 0.05.

As shown in Table 3, plants of 'Sizzle' received acceptable to excellent plant performance ratings (3.1 to 4.7) in all evaluations in the three growing seasons. The plant performance ratings of 'Sizzle' were significantly higher than those of 'Florida Red Ruffles' or 'Florida Sweetheart' in five out of nine evaluations, and were similar to the ratings of 'Florida Red Ruffles' and 'Florida Sweetheart' in three to four evaluations. 'Sizzle' did not perform as well as 'Florida Sweetheart' in only one evaluation. In full sun, leaves of 'Sizzle' turned into darker red to purple, and became more attractive.

Table 4 shows the leaf sunburn tolerance of 'Sizzle' with 'Florida Sweetheart' and 'Florida Red Ruffles' when tuber pieces were planted in ground beds and plants were grown in full sun in 2007, 2008 and 2009. Values presented are means of three replications in each year.

Leaf sun burn tolerance was evaluated on a scale of 1 to 5, with 1 being very susceptible to sun burns (leaves having numerous sun-damaged areas or holes) and 5 being resistant to sunburn (no visible sun-damaged areas). A total of nine evaluations were conducted for plant performance over three growing seasons in July, August, and September 2007, August, September, and October 2008, and August, September, and October 2009.

TABLE 4

| Cultivars | 2007 July | 2007 August | 2007 September |
|---|---|---|---|
| Sizzle | 3.7 $^{z,NS}$ | 3.6$^{NS}$ | 3.5$^{NS}$ |
| Florida Red Ruffles | 3.6 | 4.3 | 4.0 |
| Florida Sweetheart | 3.5 | 4.3 | 3.8 |

| Cultivars | 2008 August | 2008 September | 2008 October |
|---|---|---|---|
| Sizzle | 4.6 a$^{y}$ | 4.2 a | 4.6 a |
| Florida Red Ruffles | 3.9 ab | 2.3 b | 3.0 b |
| Florida Sweetheart | 3.3 b | 3.2 b | 3.5 b |

| Cultivars | 2009 August | 2009 September | 2009 October |
|---|---|---|---|
| Sizzle | 4.2 b | 5.0$^{NS}$ | 4.3 a |
| Florida Red Ruffles | 5.0 a | 5.0 | 4.7 a |
| Florida Sweetheart | 4.7 ab | 4.5 | 3.3 b |

[z]Plant sunburn tolerance was rated on a scale of 1 to 5, with 1 being very poor, 3 fair and acceptable, and 5 being excellent without showing any signs of leaf burns or holes caused by sunburn on leaf surfaces, on 27 Jul., 28 Aug., and 15 Sep. 2007; 16 Aug., 1 Sep., and 1 Oct. 2008; and 12 Aug., 15 Sep., and 8 Oct. 2009.
[y]Mean values with the same letters within columns are not significantly different at P ≤ 0.05. NS: Not significantly different at P ≤ 0.05.

As shown in Table 4, the sunburn tolerance ratings of 'Sizzle' were between 3.5 and 5.0. The sunburn tolerance ratings of 'Sizzle' were similar to those of 'Florida Sweetheart' in five evaluations and better than those of 'Florida Sweetheart' in four evaluations. The sunburn tolerance ratings of 'Sizzle' were similar to those of 'Florida Red Ruffles' in six evaluation, better than those of 'Florida Red Ruffles' in two evaluations, and slightly worse than those of 'Florida Red Ruffles' in one evaluation. 'Florida Red Ruffles' and 'Florida Sweetheart' are considered sunburn-tolerant cultivars. The sunburn tolerance ratings of 'Florida Red Ruffles' and 'Florida Sweetheart' in 2007, 2008, and 2009 ranged from 2.3 to 5.0 and from 3.2 to 4.7, respectively. These ratings suggest that 'Sizzle' has excellent sunburn tolerance.

The suitability of 'Sizzle' for pot plant production was evaluated by forcing tubers in 11.4-cm containers in spring 2008. Intact No. 1-sized tubers (>3.8 cm and <6.4 cm in diameter) were planted in a peat/vermiculite mix (VerGro Container Mix A, Verlite, Tampa, Fla.) on 17 Apr. 2008. The study was conducted in a greenhouse with 45% light exclusion. Average daily temperatures in the greenhouse ranged from a low of 16° C. at night to 29° C. during the day during the experiment. Potted plants were arranged on metal benches in the greenhouse in a randomized complete block design with eight replications. Plant height, plant width, number of leaves, and foliar characteristics were recorded on 12 Jun. 2008, 8 weeks after planting. Quality of the potted *Caladium* plants was rated on a scale of 1 to 5, 1=very poor, few leaves, totally unacceptable as potted plants, and 5=very attractive, with many bright, colorful leaves, a full plant, a symmetrical shape, and an appropriate height.

Table 5 shows a comparison of number of days to sprout, plant height, plant width, leaf number, leaf length, leaf width, and quality rating of 'Sizzle' with 'Florida Sweetheart' and 'Florida Red Ruffles'.

TABLE 5

| Cultivars | Days to sprout[z] (no.) | Plant height (cm) | Plant width (cm) | Leaves (no.) | Leaf length (cm) | Leaf width (cm) | Quality rating |
|---|---|---|---|---|---|---|---|
| 'Sizzle' | 36.9 a | 19.3$^{NS}$ | 35.8$^{NS}$ | 30.8 a$^{y}$ | 15.9 b | 9.9 c | 4.1$^{NS}$ |
| 'Florida Red Ruffles' | 35.3 | 18.3 | 35.8 | 19.1 b | 17.9 ab | 12.3 b | 3.7 |
| 'Florida Sweetheart' | 35.3 | 16.0 | 33.5 | 19.0 b | 19.2 a | 14.6 a | 3.9 |

[z]Number of days from planting to the first unfurled leaf .
[y]Mean values within columns that share the same letters are not significantly different at P ≤ 0.05. NS: Not significantly different at P ≤ 0.05.

As shown in Table 5, intact No.1-sized tubers of 'Sizzle' sprouted ~37 days after planting, similar to tubers of 'Florida Red Ruffles' and 'Florida Sweetheart' (~35 days). Potted plants of 'Sizzle' had similar heights (16.0 to 19.3 cm) and widths (33.5 to 38.5 cm) with potted plants of 'Florida Red Ruffles' and 'Florida Sweetheart'. Potted plants of 'Sizzle' produced approximately 61% more leaves than those of 'Florida Red Ruffles' and 'Florida Sweetheart.' The leaves of 'Sizzle' were 2.0 to 3.3 cm shorter and 2.4 to 4.7 cm narrower than those of 'Florida Red Ruffles' and 'Florida Sweetheart'. Pot-grown plants of 'Sizzle', 'Florida Red Ruffles', and 'Florida Sweetheart' received similar quality ratings (3.7 to 4.1).

What is claimed is:

1. A new and distinct cultivar of *Caladium* plant named 'Sizzle', as illustrated and described herein.

* * * * *